United States Patent [19]

Brehm et al.

[11] Patent Number: 5,229,466
[45] Date of Patent: Jul. 20, 1993

[54] POWDERY ABSORBING MATERIAL FOR AQUEOUS LIQUIDS BASED ON WATER-SWELLABLE CARBOXYLATE POLYMERS

[75] Inventors: Helmut Brehm; Richard Mertens, both of Krefeld, Fed. Rep. of Germany

[73] Assignee: Chemische Fabrik Stockhausen GmbH, Krefeld, Fed. Rep. of Germany

[21] Appl. No.: 884,344

[22] Filed: May 18, 1992

[51] Int. Cl.$^5$ .................. C08F 8/32; C08F 20/06
[52] U.S. Cl. .................. 525/329.9; 525/329.7; 525/380; 525/384; 525/386; 526/317.1; 528/332
[58] Field of Search .................. 525/329.9, 386, 380

[56] References Cited

U.S. PATENT DOCUMENTS 4,666,983  5/1987  Tsubakimoto .................. 525/119

FOREIGN PATENT DOCUMENTS 1706  5/1908  European Pat. Off. .
2119384  11/1983  United Kingdom .
2162525  2/1986  United Kingdom .

*Primary Examiner*—Joseph L. Schofer
*Assistant Examiner*—Fred Zitomer
*Attorney, Agent, or Firm*—Foley & Lardner

[57] ABSTRACT

The present invention relates to a powdery absorbing material for aqueous liquids based on a water-swellable powdery polymer having at least 0.2 equivalents carboxyl groups per 100 parts by weight which are neutralized by 50 to 99, advantageously by at least 80 mole %. The powdery absorbing material is obtained by treating the water-swellable carboxyl-groups-containing polymer with a solution of an N-(hydroxyalkyl)β-(meth)-alanine ester or with the polycondensation products thereof. As a solvent for the powdery absorbing material, water is used which either contains water-miscible organic diluents which evaporate on heating, or non-evaporative water-miscible organic diluents, i.e., diluents remaining in the polymer.

10 Claims, No Drawings

POWDERY ABSORBING MATERIAL FOR AQUEOUS LIQUIDS BASED ON WATER-SWELLABLE CARBOXYLATE POLYMERS

FIELD OF THE INVENTION

The present invention relates to a powdery absorbent for aqueous liquids which is based on a water-swellable polymer not setting up on contact with water or aqueous solutions, such as body liquids, i.e., said water-swellable polymers do not impede the absorption of further liquid by forming a barrier of swollen gel particles and they maintain their swelling capacity under load, as is the case when the polymers are used in diapers or incontinence articles, to a large extent.

DESCRIPTION OF BACKGROUND INFORMATION

The manufacture of water-swellable polymers is known. A typical method of producing water-swellable polymer particles by inverse suspension polymerization of an aqueous solution of acrylic acid and alkali or ammonium acrylate in a hydrocarbon, and then cross-linking the polymer is described in U.S. Pat. No. 4,698,404.

European patent application No. A1 0 205 674 describes the solvent polymerization of monomers substantially containing acid groups in the presence of an agent having a cross-linking action. After the acid groups of the polymer have been neutralized by at least 27% and the polymer gel has been dried, a water-swellable polymer is obtained which has a high gel strength and small amounts of extractable components.

European patent application No. A2 0 312 952 describes the polymerization of carboxyl-groups-containing monomers neutralized by at least 20% in the presence of dispersed cross-linking agents.

The continuous copolymerization of a monomer solution containing an acrylic acid, in which the acrylic acid is present to the extent of at least 20% in a neutralized form, is described in European Application A2 0 280 541.

In order to improve the application properties of water swelling polymers selected from the group consisting of a crosslinked hydrolysate of an acrylamidecopolymer, and a hydrolysate of a cross-linked acrylnitrilecopolymer, a crosslinked, partially neutralized acrylic acid polymers, or to adapt them to a specific application, they are frequently post-treated.

European patents 0 009 977 and 0 001 706 described the surface coating of water swelling polymers in the particle form, with hydrophobic compounds or polythers, with the purpose of improving their dispersion in blood.

U.S. Pat. No. 4,587,308 describes the post-crosslinking of water swelling polymers, dispersed in the swelled form, with diglycideethers, polyvalent metal salts or halogen-epoxy compounds.

DE-OS 34 29 379 describes a water absorbing resin, obtainable by the impregnation of a water swelling resin with a hydrophilic, reactive, olefinically unsaturated monomer or a polymer of it, and a crosslinking agent.

U.S. Pat. No. 4,666,975 describes the post-cross-linkage of water-swellable polymers in suspension by reaction with diglycide ethers.

GB 21 19 384 A claims the secondary cross-linkage in the particle surface of water-swellable polymers, the carboxyl groups of which are neutralized to 50 to 99 mol-%, with multifunctional compounds, such as polyols or polyamines.

The secondary cross-linkage in the polymer surface with solutions of polyols is described in DE-OS 35 23 617. The aftertreatment is carried out with polymers whose carboxyl groups are neutralized by 50 to 99 mol-% in the presence of water and a hydrophilic organic solvent.

All these processes strive for improving the liquid transport in a layer of polymer particles or providing a polymer which, after swelling, does not release the stored liquid on exertion of pressure, e.g., by an infant's body on the swollen polymer within a diaper. However, it is the object not only to improve the liquid transport in a layer of water-swellable polymer particles or the capability of the polymer to retain liquid under subsequent pressure when the polymer could swell freely, i.e., without load, but also to provide a water-swellable polymer which is capable of absorbing liquid even against a load. This special absorption property is referred to as absorption under pressure/load in the European Patent 0 339 461.

SUMMARY OF THE INVENTION

It has been found that water-swellable, carboxyl-groups-containing polymers 50 to 99 mol-% of which are present in neutralized form can be obtained with a high swelling capacity under load, if water-swellable polymers with a low swellability under load are treated with N-(hydroxylkyl)$\beta$-(meth)-alanine esters and/or the polycondensation products thereof and heated.

It has additionally been found that the elevated-temperature secondary treatment of carboxyl-groups-containing polymers—which are neutralized by more than 80 mol-%—with polyols or amino alcohols does not, or only under impracticable conditions, result in products with improved properties, contrast to this, treating the polymers neutralized by more than 80 mol-% with N-(hydroxyalkyl)$\beta$-(meth)-alanine esters and/or the polycondensation products thereof at elevated temperatures may result in an increase of the swelling capacity under load.

An additional technical advantage of the secondary treatment of water-swellable polymers with N-(hydroxyalkyl)$\beta$-(meth)alanine esters and/or the resulting polyamide or polyamide ethers thereof results from the fact that lower aftertreatment temperatures with a molarly identical feedstock of aftertreatment agent or shorter secondary treatment periods at the same temperature are necessary to improve the product properties. This is in contrast to the use of polyols or alkanolamines according to the and DE-OS 35 33 617.

DETAILED DESCRIPTION

The production of N-(hydroxyalkyl)$\beta$-(meth)alanine esters and their capability of forming polyamides or polyamide ethers at room temperature are described in detail in "Journal of Polymer Science", Part A-1, vol. 6, 1195–1207 (1968) and vol. 7, 889–898 (1969).

The production is carried out by the Michael reaction of alkanols or alkanolamines at (meth)acrylic acid ester.

The quantity of N-(hydroxyalkyl)$\beta$-(meth)alanine esters and/or their polycondensation products used according to the present invention amounts to 0.001 to 5 p/wt (parts by weight), relative to 100 parts of water-swellable polymer. If more than 5 p/wt are used, the extend of decrease in the swelling capacity (retention)

of the polymer is too large. Also, the swellability under load is not improved, if the charge is below 0.001 p/wt.

The aftertreatment agents according to the present invention are used in aqueous solution. The water serves to dissolve the alcohol-insoluble solid polyamides of the N-(hydroxyalkyl)β(meth)alanine esters and, at the same time, as a vehicle for incorporation of the aftertreatment agents into the water-swellable polymer particles. The quantity of water amounts to 0.1 to 5 p/wt per 100 p/wt of water-swellable polymer. Since the water-swellable polymers which have not been re-treated would set up on contact with the aqueous solutions of the after-treatment agent, additional water-soluble organic diluents are used in amounts of 0.2 to 10 p/wt per 100 p/wt of water-swellable polymer. The following substances are used as water-soluble organic diluting agents:

a) those evaporating from the solution of the secondary treatment agent and the water-swellable polymer on heating said mixture, e.g., monofunctional alcohols having 1–4 carbon atoms, acetone, glycol ether, glycol ester and/or b) those which do not evaporate on heating and remain on or in the polymer particle, e.g., butyrolactone, butyrolactam, lactic acid, and diacetin.

Since the diluents stated under a) are inflammable and form explosive mixtures which must not be emitted to the atmosphere, they require special protective measures when the secondary treatment of the water-swellable polymers is carried out.

The diluents stated under b) remain on the polymer and do not require special protective measures. However, they may negatively influence the swelling capacity of the aftertreated polymers, when used in larger amounts during the secondary treatment.

The amount of added water-soluble organic diluting agent depends on the amount of water employed. The quantity should be determined such that, after mixing with the water-swellable polymer, a product results which is easy to handle and does not contain agglutinated particles.

The solution of the preparation is mixed with the powdery, water-swellable, carboxy-groups-containing polymer and subsequently heated. The powdery polymer may have a spherical shape, obtainable by polymerization of emulsified aqueous monomer solutions, or an irregular shape, obtainable by solvent polymerization, e.g., of a 30% monomer solution comprising 50 to 99 mol-% alkali acrylate, 50 to 1 mol-% acrylic acid and 0.01 to 0.5%-wt. of an agent having a cross-linking action. The particle size of the water-swellable polymer to be treated amounts to 0.05 to 1 mm, preferably 0.1 to 0.8 mm.

The mixture consisting of the solution of the agent and the water-swellable polymer is manufactured in the laboratory with ordinary mixers, such as those used in the household. In large-scale production, blade mixers or paddle mixers operating continuously or discontinuously are used. The solution of the agent is evenly dosed to the powder preparation or into the powder stream.

The mixture of dissolved, diluted preparation and water-swellable polymer is subsequently heated to 100° to 250° C., preferably 150° to 210° C. The heating temperature and time depend on the amount of agent, and the treatment time in general is between at least 5 min. and one hour.

The amount of preparation, the mode of feeding, and the treatment temperature are advantageously coordinated in such a way that the duration of treatment permits a continuous performance of the process, i.e., the required heat-up time is not too long resulting in lengthy dwell times within the dryer and the subsequent cooler. Suitable dryers are, e.g., the drying cabinet or the disk dryer.

A water-swellable polymer giving a dry impression after the swelling, not impairing the advance of liquid by forming a barrier, and swelling against external load with a high swelling capacity (retention) is obtained. Therefore, the polymer according to the present invention is particularly suitable for embedding it between paper, non-woven fabrics and in diaper constructions. The aftertreated polymer obtained is examined as follows:

1. Liquid absorption

The absorbed amount of liquid per gram of water-swellable polymer is measured. A weighed polymer quantity is enclosed in a tea bag and dipped into a 0.9% solution of sodium chloride. The amount of absorption is determined after 10 minutes, after the tea bag has been centrifuged at 1400 rpm for 5 minutes in a centrifuge having a diameter of 23 cm; the liquid amount absorbed by the tea bag material is deducted.

$$\text{Amount of absorption (retention)} \left(\frac{g}{g}\right) = \frac{\text{weight after absorption (g)} - \text{weight of the tea bag (g)}}{\text{weight of the polymer (g)}}$$

2. Liquid absorption under load

The absorption under load (AUL) is determined according to the method described in European Patent No. 0 339 461, page 7:

The weighed portion of superabsorber is placed in a cylindrical vessel with sieve bottom and the powder is stressed with a punch exerting a pressure of 20 g/cm². The cylinder is subsequently placed on a Demand-Absorbency-Testing Device (DAT) and the superabsorber is allowed to suck 0.9% NaCl-solution for one hour.

3. Modulus of shear

The modulus of shear is measured by means of a Carri-Med-Stress-Rheometer with plate-plate-configuration. In order to determine the modulus of shear 1 g water-absorbing resin is allowed to swell for one hour in 28 g 0.9% NaCl-solution, then the modulus of shear is measured in the swollen gel in dependence of the frequency (0.1–10 Hz). The value at 10 Hz is indicated as storage modulus G' in N/m².

The present invention will be illustrated in more detail by the following examples.

1. Production of the agents used according to the present invention for the water-swellable polymers (N-(hydroxyalkyl)β-(meth)-alanine esters and the polycondensation products thereof:

a) Agent A 10 g ethyl acrylate and 10 g ethanol are weighed into a flask and 6.15 g ethanolamine are added under stirring. The solution which is warming up is allowed to stand for 15 hours to terminate reaction.

b) Agent B 10 g methyl methacrylate and 6.15 g ethanolamine are reacted at 40° C. for 15 hours under stirring.

c) Agent C

In a flask 13 g 2-hydroxypropyl acrylate and 10 g ethanol are stirred-up with 6.2 g ethanolamine at room temperature. The solution is allowed to stand for 18 hours to terminate reaction.

d) Agent D

Preparation A, which is a clear solution, is allowed to stand for 14 days at room temperature. During this period, a fine white precipitate forms which is soluble in alcohol or water. The homogenized suspension is used to treat the polymers.

a single-armed domestic mixer with aftertreatment agents, water, and organic diluting agents (the amounts are stated in Table 1) within about 3 min. The mixture is spread in a glass dish at a layer thickness of 5 to 10 mm and heated in a recirculating air dryer. The drying periods and temperatures as well as the test results are stated in Table 1. Ethanolamine and glycerol were used as preparation agent in the comparative examples 1 to 3.

TABLE 1

|  | Water (g) | Diluent (g) | Agent (g) | Time (min) | Temp. (°C.) | AUL (g/g) | Retention (g/g) |
|---|---|---|---|---|---|---|---|
| Exam. No. |  |  |  |  |  |  |  |
| 1 | 2.0 | methanol 2.8 | E 1.3 | 10 | 190 | 24.0 | 32.6 |
| 2 | 2.0 | methanol 2.4 | A 1.0 | 20 | 190 | 30.9 | 33.2 |
| Comparative Example |  |  |  |  |  |  |  |
| 1 | 2.0 | methanol 2.8 | ethanolamine 0.5 | 10 | 190 | 6.9 | 39.6 |
|  | " | " | " | 20 | 190 | 7.5 | 40.7 |
| 2 | 2.0 | methanol 2.8 | glycerol 0.5 | 20 | 190 | 8.2 | 38.1 |
|  | " | " | " | 60 | 190 | 8.6 | 39.6 |
| 3 | 2.0 | 2.8 | 1.0 | 30 | 190 | 13.8 | 37.9 | e) Agent E 100 g ethyl acrylate and 100 g ethanol are mixed in an agitated flask with 61 g ethanolamine; after 18 hours in a rotary evaporator at a bath temperature of 80° C. and a pressure of 20 mbar, the clear solution is liberated from volatile components. An oil which is slightly turbid at room temperature and highly viscous is obtained which becomes waxy during standing.

f) Agent F 100 g ethyl acrylate are added to 61 g monoethanolamine in 200 ml methanol within an agitated flask, and the mixture is stirred for 8 hours. 800 ml methanol and 14 g 25% potassium methylate solution are added into the agitated flask and stirring is continued for 80 hours. The resulting white precipitate is filtered off, stirred up in 500 ml methanol and filtered off once again. The filter cake is dried at 50° C. and 25 mbar.

73.2 g white powder are obtained, and the white powder melts between 195° and 203° C.

g) Agent G 1000 ml tetrahydrofuran are placed in an agitated flask; 14 g 25% potassium methylate solution, 62 g monoethanolamine and 100 g ethyl acrylate are added under stirring. The initially clear solution becomes cloudy and then a soft polycondensate settles down at the bottom of the reactor. The supernatant solution is poured off and the viscous polycondensate is liberated from adhering volatile components at 25 mbar and 50° C. Total amine: 2.8 mmol/g.

2) Treatment of the water-swellable polymers according to the present invention:

EXAMPLE 1 AND 2 AND COMPARATIVE EXAMPLES 1 TO 3:

A water-swellable polymer having a particle size of 0.2 to 0.8 mm is obtained by polymerizing a 29% monomer solution of 90 mol-% sodium acrylate and 10 mol-% acrylic acid in the presence of 0.25%-wt. trimethylol-propane-triacrylate (relative to acrylic acid) having an absorbency (retention) for 0.9% NaCl-solution of 40.0 g/g and an absorbency under load (AUL) of 6.9 g/g.

100 g of the water-swellable polymer are placed in a 500 ml plastic cup and mixed under strong stirring with

EXAMPLES 3 TO 5

A polymer with the grain size 0.15 to 0.8 mm is obtained by solvent polymerization as in Example 1, except for the fact that the monomer mixture consisted of 70 mol-% of sodium acrylate and 30 mol-% of acrylic acid. The polymer has a retention of 39.5 g/g and an AUL of 7.6 g/g.

100 g of this powdery polymer are mixed with solutions of the preparation F as in Example 1 and heated. The treatment conditions and test results are listed in Table 2.

TABLE 2

| Exam. No. | Water (g) | Diluent (g) | Agent (g) | Time (min) | Temp. (°C.) | AUL (g/g) | Retention (g/g) |
|---|---|---|---|---|---|---|---|
| 3 | 2.0 | methanol 2.8 | 0.30 | 15 | 180 | 25.8 | 37.3 |
| 4 | 2.0 | methanol 2.8 | 0.15 | 15 | 180 | 28.6 | 37.6 |
| 5 | 2.0 | ethanol 2.8 | 0.05 | 20 | 190 | 32.6 | 38.1 |

EXAMPLE 6

100 g of the water-swellable polymer used in Example 3 are mixed with a solution of 0.1 g of agent E, 2 g water, and 1.0 g 2-pyrrolidone as in Example 1 and heated.

| Treatment | | AUL (g/g) | Retention (g/g) |
|---|---|---|---|
| temp. (°C.) | time (min) | | |
| 190 | 10 | 26.2 | 40.4 |
| 190 | 15 | 30.4 | 36.2 |
| 190 | 20 | 29.2 | 34.9 |

EXAMPLES 7 TO 12 AND COMPARATIVE EXAMPLE 4

The mixture is prepared with 100 g polymer according to Example 3, the conditions, secondary treatment agents, treatment temperatures and times are stated in Table 3.

TABLE 3

| Exam. No. | Water (g) | Solvent (g) | Agent (g) | Temp. (°C.) | Time (min) | AUL (g/g) | Retention (g/g) |
|---|---|---|---|---|---|---|---|
| | | | A | | | | |
| 7 | 2.0 | — | 8.58 | 150 | 10 | 27.9 | 39.0 |
| | | methanol | A | | | | |
| 8 | 2.0 | 2 | 2.11 | 180 | 10 | 30.3 | 34.1 |
| | | methanol | A | | | | |
| 9 | 2.0 | 2 | 1.05 | 180 | 14 | 31.1 | 36.0 |
| | | methanol | A | | | | |
| 10 | 2.0 | 2 | 0.52 | 180 | 20 | 28.7 | 36.1 |
| | | methanol | B | | | | |
| 11 | 2.0 | 2 | 5.27 | 150 | 60 | 31.3 | 35.4 |
| | | ethanol | C | | | | |
| 12 | 2.0 | 2 | 2.4 | 150 | 30 | 27.3 | 33.6 |
| Comparative Example | | | | | | | |
| | | ethanol | ethanolamine | | | | |
| 4 | 2.0 | 3.85 | 0.5 | 150 | 30 | 9.0 | |
| | 2.0 | 3.85 | 0.5 | 150 | 60 | 10.5 | |

EXAMPLE 13

100 g of the water-swellable polymer used in Example 3 ($G' = 1800$ N/m$^2$) are mixed with 5.05 g of a solution of 1.05 g of the homogenized suspension of after-treatment agent D, 2.0 g water, and 2.0 g methanol and heated in the recirculating air dryer.

| Treatment time (min) | temp. (°C.) | AUL (g/g) | Retention (g/g) | G' (N/m$^2$) |
|---|---|---|---|---|
| 10 | 180 | 26.8 | 36.7 | 2350 |

EXAMPLES 14 TO 16

100 g of a cross-linked polyacrylic acid, the carboxyl groups of which are present in neutralized form by 60 mol-%, and having a particle size of 0.2 to 0.85 mm, tradename FAVOR 922 of Chemische Fabrik Stockhausen GmbH, Krefeld, FRG, are mixed with a solution of preparation A in 2.0 g water and 2.0 g water and 2.0 g methanol as in Example 1 and heated in a recirculating air dryer.

| Exam. No. | Agent (g) | Temp. (°C.) | Time (min) | AUL (g/g) | Retention (g/g) |
|---|---|---|---|---|---|
| FAVOR | — | — | — | 9.3 | 41.9 |
| 14 | 2.1 | 180 | 10 | 25.1 | 30.2 |
| 15 | 4.2 | 160 | 10 | 26.4 | 34.5 |
| 16 | 4.2 | 150 | 15 | 28.2 | 34.1 |

EXAMPLE 17

1500 g water-swellable polymer of the particle size 0.15 to 0.85 mm, manufactured by polymerization of a 29% solution of 70 mol-% sodium acrylate, 30 mol-% acrylic acid and 0.17%-wt. of trimethylol-propane-triacrylate (relative to acrylic acid) with a retention of 44.8 g/g and an AUL of 7.2 g/g are prepared in a Draismixer. A solution of 1.5 g agent E, 30 g water, and 15 g 2-pyrrolidone is added dropwise into the moved powder bed. The resulting mixture is heated in a free-falling mixer which has been preheated to 210° C. The heating-up times, temperatures, and the test results are listed in Table 4.

TABLE 4

| Time (min) | Temperature (°C.) | AUL (g/g) | Retention (g/g) |
|---|---|---|---|
| 10 | 146 | heating-up period | |
| 20 | 177 | | |
| 25 | 183 | — | — |
| 30 | 183 | 30.2 | 40.4 |
| 40 | 185 | 29.6 | 38.6 |
| 50 | 186 | 28.7 | 37.8 |

EXAMPLE 18

100 g of the water-swellable polymer used in Example 3 are mixed with a solution of 0.3 g agent G in 2.0 g water and 2.8 g methanol; the mixture is spread out in a glass dish and stored in a drying cabinet of 190° C. for 15 min. The product cooled to room temperature does not block during the swelling, has an AUL of 33.5 g/g and a retention of 37.7 g/g.

EXAMPLE 19

100 g of the water-swellable polymer used in Example 3 are mixed with a solution of 0.1 g agent E in 2.0 g water and 1.0 g diacetin. The powdery product is placed in a drying cabinet preheated to 190° C. After cooling, an AUL of 29.9 g/g is measured.

EXAMPLE 20

A cross-linked, water-swellable polymer having a particle size of 0.15 to 0.80 mm and the composition according to Example 3 is used. The polymer has a retention of 35.5 g/g, an AUL of 9.4 g/g and a storage modulus of 2600 N/m$^2$.

A mixture of 1.5 g preparation, manufactured like agent A without using ethanol as diluent, 30 g water and 30 g diacetin is mixed as described in Example 17 with 1500 g of the powdery polymer and heated. After a treatment period of 20 min at 183° to 185° C., the polymer exhibits the following characteristics:

Retention = 30.7 g/g
AUL = 31.1 g/g
$G' = 5300$ N/m$^2$.

EXAMPLE 21

100 g of a cross-linked polyacrylic acid, the carboxyl groups of which are present in neutralized form by 70 mol-%, and having a retention of 47.5 g/g and an AUL of 8.4 g/g, are treated with 4.1 g of the treatment mixture according to Example 20 and stored at a layer thickness of 3 mm in a drying cabinet preheated to 240° C. for 10 min. The obtained polymer has a retention of 35.5 g/g and an AUL of 24.4 g/g.

It is understood that the specification and examples are illustrative but not limitative of the present invention and that other embodiments within the spirit and scope of the invention will suggest themselves to those skilled in the art.

What is claimed is:

1. A powdery absorbent for aqueous liquids which is based on a water-swellable powdery polymer produced by heating a mixture consisting of:
   a) 100 parts by weight of at least one water-swellable, carboxyl-groups-containing polymer comprising at least 0.2 equivalents of carboxyl groups per 100 parts by weight, 50 to 99 mol % of which are present in neutralized form; b) 0,001 to 5 parts by weight N-(hydroxyalkyl)$\beta$-(meth)-alanine esters, or polycondensation products thereof;
   c) 0.01 to 5 parts by weight water; and
   d) 0.2 to 10 parts by weight of a water-miscible organic diluting agent which evaporates on heating the mixture and/or 0.2 to 10 parts by weight of a water-miscible organic diluent which does not evaporate on heating the mixture.

2. The powdery absorbent according to claim 1 obtained by heating the mixture according to claim 1 to 100° to 250° C., preferably to 150° to 210° C.

3. The powdery absorbent according to claim 1 obtained by the use of $\beta$-(meth)-alanine esters substituted at the nitrogen atom by hydroxy-$C_1$-$C_6$-alkyl groups.

4. The powdery absorbent according to claim 1 obtained by using N-(hydroxyalkyl)-substituted $\beta$-(meth-)alanine-$C_1$-$C_6$-alkyl esters or -$C_1$-$C_6$-hydroxyalkyl esters.

5. The powdery absorbent according to claims 1 obtained by using water-soluble polyamides of N-(hydroxyalkyl)$\beta$(meth)-alanine esters.

6. The powdery absorbent according to claim 1 obtained by using water-soluble polyamide ethers of N-(hydroxyalkyl)$\beta$-(meth-)alanine esters.

7. The powdery absorbent according to claim 1 in which at least 80 mol-% of the polymer are neutralized.

8. The powdery absorbent according to claim 1, wherein said N-(hydroxyalkyl)$\beta$-(meth)-alanine esters, or polycondensation products thereof are present in an amount of 0.05 to 2 parts by weight.

9. The powdery absorbent according to claim 1 wherein said water miscible organic diluting agent which evaporates on heating is selected from the group consisting of monofunctional alcohols having from 1–4 carbon atoms, acetone, glycol ether and glycol ester.

10. A powdery agent according to claim 1, wherein said water-miscible organic diluent which does not evaporate on heating is selected from the group consisting of butyrolactone, butyrolactam, lactic acid and diacetin.

* * * * *